United States Patent [19]

deFraine et al.

[11] Patent Number: 5,336,682
[45] Date of Patent: * Aug. 9, 1994

[54] HETEROCYCLIC COMPOUNDS AS FUNGICIDES

[75] Inventors: Paul deFraine, Wokingham; Brian K. Snell, Reading; Kevin Beautement, Wokingham; Vivienne M. Anthony, Maidenhead; John M. Clough, Marlow, all of United Kingdom

[73] Assignee: Imperial Chemical Industries Public Limited Company, London, United Kingdom

[ * ] Notice: The portion of the term of this patent subsequent to Feb. 25, 2009 has been disclaimed.

[21] Appl. No.: 804,991

[22] Filed: Dec. 10, 1991

Related U.S. Application Data

[60] Division of Ser. No. 442,436, Nov. 24, 1989, Pat. No. 5,091,407, which is a continuation of Ser. No. 872,687, Jun. 10, 1986, abandoned.

[30] Foreign Application Priority Data

Jun. 18, 1985 [GB] United Kingdom ............ 8515385
Apr. 17, 1986 [GB] United Kingdom ............ 8609453

[51] Int. Cl.$^5$ ............ A01N 43/36; C07D 407/06
[52] U.S. Cl. ............ 514/422; 548/517; 548/518; 548/527
[58] Field of Search ............ 548/527, 518, 517; 514/422

[56] References Cited

U.S. PATENT DOCUMENTS 5,091,407  2/1992  deFraine et al. ............ 514/423

*Primary Examiner*—Joseph P. Brust
*Attorney, Agent, or Firm*—Cushman, Darby & Cushman

[57] ABSTRACT

Fungicidally active compounds of the formula

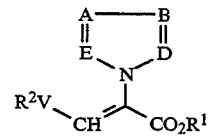

and stereoisomers thereof, wherein A is the group =CW— or a nitrogen atom, B is the group =CX— or a nitrogen atom, D is the group =CY— or a nitrogen atom, and E is the group =CZ— or a nitrogen atom, wherein W, X, Y and Z, which may be the same or different, are, for example, hydrogen, halogen, nitro, nitrile, or other defined groups and wherein $R^1$ and $R^2$ are alkyl, cycloalkyl, alkenyl, alkynyl, optionally substituted aryl, optionally substituted aralkyl, cycloalkyl groups, or optionally substituted heteroaromatic, and V is oxygen or sulfur.

6 Claims, No Drawings

HETEROCYCLIC COMPOUNDS AS FUNGICIDES

This is a division of application Ser. No. 07/442,436, filed Nov. 24, 1989, now U.S. Pat. No. 5,091,407, which is a continuation of Ser. No. 06/872,687, filed Jun. 10, 1986, now abandoned.

This invention relates to derivatives of acrylic acid useful as fungicides, to processes for preparing them, to fungicidal compositions containing them, and to methods of combating fungi, especially fungal infections in plants, using them.

The invention provides a compound having the general formula (I):

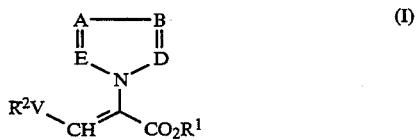

and stereoisomers thereof, wherein A is the group =CW— or a nitrogen atom, B is the group =CX— or a nitrogen atom, D is the group =CY— or a nitrogen atom, and E is the group =CZ— or a nitrogen atom, wherein W, X, Y and Z, which may be the same or different, are hydrogen or halogen atoms, or nitro, nitrile, the group

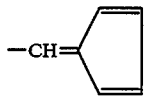

or any of the following, optionally substituted groups namely alkyl, cycloalkyl, cycloalkylalkyl, alkenyl, alkynyl, aryl, aralkyl, arylazo, alkoxy, heterocyclyloxy, aryloxy, aryloxyalkyl, amino, acylamino or the groups $CO_2R^3$, $CONR^4R^5$, $COR^6$ or $S(O)_nR^7$ (where n=0, 1, or 2) or $CR^8=NR^9$; and wherein $R^1$, $R^2$, $R^3$, $R^4$, $R^5$, $R^6$, $R^7$ and $R^8$, which may be the same or different, are hydrogen atoms, but $R^1$ and $R^2$ are not hydrogen, or alkyl, cycloalkyl, alkenyl, alkynyl, optionally substituted aryl, optionally substituted aralkyl, cycloalkyl groups or optionally substituted heteroaromatic (which can contain O, N or S atoms in a 5 or 6 membered ring e.g. thiophene, furan, pyridyl or pyrimidinyl), whilst $R^9$ may be alkyl, cycloalkyl optionally, substituted aryl, optionally substituted aralkyl or cycloalkylalkyl or optionally substituted aromatic heterocyclyl. V can be either oxygen or sulphur.

The compounds of the invention contain at least one carbon-carbon double bond, and are sometimes obtained in the form of mixtures of geometric isomers. However, these mixtures can be separated into individual isomers, and this invention embraces such isomers individually and as mixtures.

A, B, E, and D are groups which, taken together with the N-atom, constitute a pyrrole, pyrazole, imidazole, triazole or tetrazole ring.

Preferred alkyl groups for W, X, Y, Z and $R^1$ to $R^9$ contain from 1 to 6, especially 1 to 4, carbon atoms, and can be straight or branched chain alkyl groups having 1 to 6, e.g. 1 to 4 carbon atoms; examples are methyl, ethyl, propyl (n- or iso-propyl) and butyl (n-, sec-, iso- or t-butyl).

$R^1$ and $R^2$ are preferably both methyl.

Preferred cycloalkyl groups for $R^1$ to $R^9$ contain from 3 to 6 carbon atoms, e.g. cyclopropyl, cyclobutyl, cyclopentyl, and cyclohexyl. Preferred alkenyl and alkynyl groups for $R^1$ to $R^8$ and W, X, Y and Z contain up to 7 carbon atoms and preferably up to 4 carbon atoms; and include allyl and propargyl.

When any of W, X, Y and Z, and $R^1$ to $R^9$ are, or include, aryl, e.g. phenyl, it may be unsubstituted, or substituted with 1, 2 or 3 ring substituents at the 2-, 3- or 4 positions of the ring which may be the same or different. Examples of aryl groups are phenyl, 2-, 3-, or 4-chlorophenyl, 2,4- or 2,6-dichlorophenyl, 2,4- or 2,6-difluorophenyl, 2-, 3- or 4-fluorophenyl, 2-, 3- or 4-bromophenyl, 2-, 3- or 4-methoxyphenyl, 2,4-dimethoxyphenyl, 2-, 3 - or 4 -ethoxyphenyl, 2- fluoro-4-chorophenyl, 2-chloro-4-fluorophenyl, 2-, 3- or 4-methylphenyl, 2-, 3- or 4-ethylphenyl, 2-, 3- or 4-trifluoromethylphenyl, 4-phenyl-phenyl (4-biphenylyl), 2-chloro-4-methoxyphenyl, 2-fluoro-4-methoxyphenyl, 2-chloro-4-methylphenyl, 2- fluoro-4-methylphenyl, 4-isopropylphenyl.

When $R^9$ is cycloalkylalkyl it may be, for example, comprised of any cycloalkyl moiety containing from 3 to 6 carbon atoms combined with an alkyl moiety containing from 1 to 6 carbon atoms and specific cycloalkyl and alkyl moieties are those specified above.

In a further aspect the invention provides compounds according to general formula I wherein W, X, Y and Z are hydrogen, halogen, nitro, nitrile, $C_{1-4}$ alkyl, $C_{3-6}$ alkenyl, $C_{3-6}$ alkynyl, aryl, aryl$_{1-4}$alkyl, arylazo, $C_{1-4}$ alkoxy, heterocyclyloxy, aryloxy, aryloxy$C_{1-4}$alkyl, or $COOR^3$, $CONR4R^5$ $COR^6$, or $S(O)_nR^7$ where n is 0, 1 or 2, or $CR^7=NR^8$ wherein $R^1$, $R^2$, $R^3$, $R^4$, $R^5$, $R^6$, $R^7$, $R^8$ are $C_{1-4}$ alkyl, $C_{3-6}$ cycloalkyl, $C_{3-4}$ alkenyl, $C_{3-4}$ alkynyl, or are an optionally substituted group which is aryl, aryl $C_{1-4}$alkyl, $C_{3-6}$cycloalkyl, pyrrole, imidazole, pyrazole, 1,2,3-triazole, 1,2,4-triazole or tetrazole, and $R^9$ is $C_{1-4}$ alkyl, $C_{3-6}$ cycloalkyl or an optionally substituted group which is aryl aryl$C_{1-4}$alkyl, or $C_{3-6}$ cycloalkyl$C_{1-4}$alkyl; and V is oxygen.

In a yet further aspect the invention provides compounds having the general formula I wherein $R^1$ and $R^2$ are both methyl and the moiety:

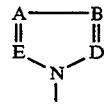

is a substituted ring which is a pyrrole, imidazole, pyrazole, 1,2,3-triazole, 1,2,4-triazole, or 1,3,4-triazole ring.

In a still further aspect the invention provides compounds having the general formula I wherein $R^1$ and $R^2$ are both methyl and the moiety:

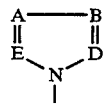

is a pyrrole, imidazole, pyrazole, 1,2,3-triazole, 1,2,4-triazole, or 1,3,4-triazole ring; and wherein E is a carbon atom bearing directly, or through a linking group which is —CH=CH—, —CO—, =CH—, —S—, —SO—, —O—CO—, —CH$_2$—O—, —O—CH$_2$—, —O—CH$_2$—CO—, —CH$_2$— or —CH$_2$—CH$_2$—; any of cyano (i.e. CN), $C_{1-4}$alkyl, halogen, nitro, phenyl; pyridyl, thienyl, pyrrol and piperidine all optionally substituted with $C_{1-4}$ alkyl, $C_{1-4}$ alkoxy, halogen, halo$C_{1-4}$alkyl, $C_{3-6}$ cycloalkyl, $C_{3-6}$ cycloalkenyl, or biphenylyl.

In another aspect the invention provides compounds having the formula:

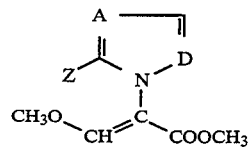

wherein A is =CH—, or =N—, D is =CH— or =N—; and Z is cyano (i.e. CN), $C_{1-4}$ alkyl, halogen, nitro, phenyl, pyridyl, thienyl, pyrrolyl or piperidine all optionally substituted with $C_{1-4}$alkyl, $C_{1-4}$alkoxy, halogen, halo$C_{1-4}$alkyl, $C_{3-6}$ cycloalkyl, $C_{3-6}$ cycloalkenyl, or biphenylyl; the group Z being linked directly to the ring carbon atom or through —CH=CH—, —CO—, =CH—, —S—, —SO—, —O—CO—, —CO—O—, —O—CH$_2$—, —O—CH$_2$—CO—, —CH$_2$—, or —CH$_2$—CH$_2$—, thereto.

In yet another aspect the invention provides compounds having the formula:

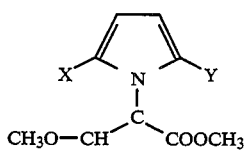

wherein X is CN, $C_{1-4}$ alkoxy carbonyl, phenacyl wherein the phenyl ring thereof is optionally substituted at the 2-, 3- or 4-position with halogen, $C_{1-4}$ alkyl, or halo$C_{1-4}$alkyl, styryl, theinylcarbonyl, or pyridylthio; and Y is hydrogen, $C_{1-4}$ alkyl, or nitro.

In particular the invention provides the compounds having the structural formula:

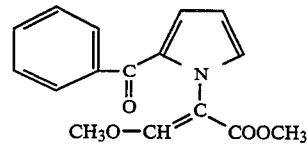

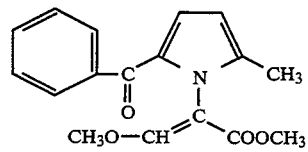

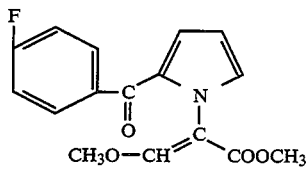

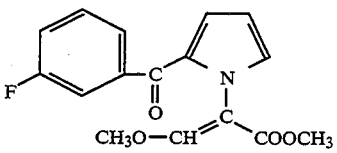

TABLE I

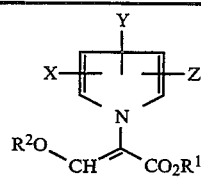

| Compound No. | $R^1$ | $R^2$ | X | Y | Z | Melting point (°C.) | olefinic* | isomer+ |
|---|---|---|---|---|---|---|---|---|
| 1 | CH$_3$ | CH$_3$ | 2-(E—C$_6$H$_5$CH=CH) | H | H | 126–128 | 7.71 | Z |
| 2 | CH$_3$ | CH$_3$ | 2-C$_6$H$_5$CO | H | H | 78–79 | 7.49 | Z |
| 3 | CH$_3$ | CH$_3$ | 2-CN | H | H | 97 | 7.67 | Z |
| 4 | CH$_3$ | CH$_3$ | 2-C$_6$H$_5$CH$_2$ | H | H | | | Z |
| 5 | CH$_3$ | CH$_3$ | 2-C$_5$H$_{11}$ | H | H | | | Z |
| 6 | CH$_3$ | CH$_3$ | 2-C$_6$H$_5$CH$_2$CH$_2$ | H | H | | | Z |
| 7 | CH$_3$ | CH$_3$ | 2-C$_6$H$_5$N(Me)CO | H | H | | | Z |
| 8 | CH$_3$ | CH$_3$ | 2-(cyclopentenyl)=CH— | H | H | | | Z |
| 9 | CH$_3$ | CH$_3$ | 3-C$_6$H$_5$CO | H | H | Oil | 7.57 | Z |
| 10 | CH$_3$ | CH$_3$ | 2-(4-ClC$_6$H$_4$CO) | H | H | 127–128 | 7.55 | Z |
| 11 | CH$_3$ | CH$_3$ | 2-C$_6$H$_5$CO | 5-CH$_3$ | H | 77–80 | 7.58 | Z |
| 12 | CH$_3$ | CH$_3$ | 2-(4-CH$_3$OC$_6$H$_4$CO) | H | H | 116 | 7.46 | Z |
| 13 | CH$_3$ | CH$_3$ | 2-(2,4-Cl$_2$C$_6$H$_3$CO) | H | H | 124–125 | 7.48 | Z |
| 14 | CH$_3$ | CH$_3$ | 2-(4-FC$_6$H$_4$CO) | H | H | 74 | 7.45 | Z |
| 15 | CH$_3$ | CH$_3$ | 2-(2-FC$_6$H$_4$CO) | H | H | Oil | 7.46 | Z |
| 16 | CH$_3$ | CH$_3$ | 2-(4-$^t$C$_4$H$_9$C$_6$H$_4$CO) | H | H | 111 | 7.46 | Z |
| 17 | CH$_3$ | CH$_3$ | 2-(4-CF$_3$C$_6$H$_4$CO) | H | H | 127 | 7.55 | Z |
| 18 | CH$_3$ | CH$_3$ | 2-(2-C$_5$H$_4$N—S) | H | H | 79 | 7.53 | Z |
| 19 | CH$_3$ | CH$_3$ | 2-(2-C$_5$H$_4$N—SO) | H | H | 157–159 | | Z |
| 20 | CH$_3$ | CH$_3$ | 2-CH$_3$OCO | H | H | 76–78 | 7.50 | Z |
| 21 | CH$_3$ | CH$_3$ | 2-$^t$C$_4$H$_9$CO | H | H | Oil | 7.40 | Z |

TABLE I-continued

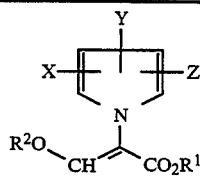

| Compound No. | R¹ | R² | X | Y | Z | Melting point (°C.) | olefinic* | isomer+ |
|---|---|---|---|---|---|---|---|---|
| 22 | $CH_3$ | $CH_3$ | 2-(4-$CH_3C_6H_4CO$) | H | H | 117–118 | 7.46 | Z |
| 23 | $CH_3$ | $CH_3$ | 2-(2-$ClC_6H_4CO$) | H | H | Oil | 7.46 | Z |
| 24 | $CH_3$ | $CH_3$ | 2-(2-$C_4H_3S$—CO) | H | H | 81–83 | 7.47 | Z |
| 25 | $CH_3$ | $CH_3$ | 2-(3,5-$Cl_2C_6H_3CO$) | H | H | 143–144 | | Z |
| 26 | $CH_3$ | $CH_3$ | 2-(2,6-$Cl_2C_6H_3CO$) | H | H | 96–97 | 7.57 | Z |
| 27 | $CH_3$ | $CH_3$ | 2-(3-$FC_6H_4CO$) | H | H | Oil | 7.44 | Z |
| 28 | $CH_3$ | $CH_3$ | 2-(3-$ClC_6H_4CO$) | H | H | 108 | 7.44 | Z |
| 29 | $CH_3$ | $CH_3$ | 2-$^nC_3H_7OCO$ | H | H | Oil | 7.50 | Z |
| 30 | $CH_3$ | $CH_3$ | 2-$^iC_4H_9OCO$ | H | H | Oil | 7.37 | Z |
| 31 | $CH_3$ | $CH_3$ | 2-$C_6H_5CH_2OCO$ | H | H | | | Z |
| 32 | $CH_3$ | $CH_3$ | 2-$C_6H_5OCO$ | H | H | | | Z |
| 33 | $CH_3$ | $CH_3$ | 2-$C_6H_5COCO$ | H | H | | | Z |
| 34 | $CH_3$ | $CH_3$ | 2-(2-$C_4H_3O$—CO) | H | H | 85–6 | 7.50 | Z |
| 35 | $CH_3$ | $CH_3$ | 2-(2-$C_5H_5N$—CO) | H | H | | | Z |
| 36 | $CH_3$ | $CH_3$ | 2-$C_6H_5S$ | H | H | | | Z |
| 37 | $CH_3$ | $CH_3$ | 2-$C_6H_5CO$ | H | 5-CN | | | Z |
| 38 | $CH_3$ | $CH_3$ | 2-$C_6H_5CO$ | H | 5-$CO_2CH_3$ | | | Z |
| 39 | $CH_3$ | $CH_3$ | 2-$C_5H_{10}N$—$CH_2$ | H | H | | | Z |
| 40 | $CH_3$ | $CH_3$ | 2-(3-$CH_3C_6H_4CO$) | H | H | 110–1 | 7.51 | Z |
| 41 | $CH_3$ | $CH_3$ | 2-(4-$FC_6H_4CH_2$) | H | H | | | Z |
| 42 | $CH_3$ | $CH_3$ | 2-(4-$FC_6H_4CH_2CH_2$) | H | H | | | Z |
| 43 | $CH_3$ | $CH_3$ | 2-(3-$C_4H_3S$—CO) | H | H | 130–1 | 7.50 | Z |
| 44 | $CH_3$ | $CH_3$ | 2-(3-$C_4H_3O$—CO) | H | H | | | Z |
| 45 | $CH_3$ | $CH_3$ | 2-(3-$C_5H_4N$—CO) | H | H | | | Z |
| 46 | $CH_3$ | $CH_3$ | 2-[2-(5-Cl—$C_5H_3N$)CO] | H | H | | | Z |
| 47 | $CH_3$ | $CH_3$ | 4-$FC_6H_5OCO$ | H | H | | | Z |
| 48 | $CH_3$ | $CH_3$ | 2-$C_6H_5OCH_2$ | H | H | | | Z |
| 49 | $CH_3$ | $CH_3$ | 2-$C_6H_5CHCH_3$ | H | H | | | Z |
| 50 | $CH_3$ | $CH_3$ | 2-$C_3H_7CHCH_3$ | H | H | | | Z |
| 51 | $CH_3$ | $CH_3$ | 2-$(CH_3)_2CHOCO$ | H | H | | | Z |
| 52 | $CH_3$ | $CH_3$ | 2-$C_6H_5CO$ | $3CH_3$ | H | | | Z |
| 53 | $CH_3$ | $CH_3$ | 2-$C_6H_5CO$ | $4CH_3$ | H | | | Z |
| 54 | $CH_3$ | $CH_3$ | 2-(3-$CH_3OC_6H_4CO$) | H | H | 92–3 | 7.53 | Z |
| 55 | $CH_3$ | $CH_3$ | H | H | H | 88–9 | 7.51 | Z |
| 56 | $CH_3$ | $CH_3$ | 2-[3-(6-Cl—$C_5H_3N$)CO] | H | H | | | Z |
| 57 | $CH_3$ | $CH_3$ | 2-[2-(5-Br—$C_5H_3N$)CO] | H | H | | | Z |
| 58 | $CH_3$ | $CH_3$ | 2-(3-$CNC_6H_4CO$) | H | H | | | Z |
| 59 | $CH_3$ | $CH_3$ | 2-(3,5-$F_2C_6H_3CO$) | H | H | | | Z |
| 60 | $CH_3$ | $CH_3$ | 2-($C_6H_5OCH_2CO$) | H | H | | | Z |
| 61 | $CH_3$ | $CH_3$ | 2-(4-$FC_6H_4OCH_2CO$) | H | H | | | Z |
| 62 | $CH_3$ | $CH_3$ | 2-(3,5-di-$CH_3OC_6H_3CO$) | H | H | | | Z |
| 63 | $CH_3$ | $CH_3$ | 2-(3-$NO_2C_6H_4CO$) | H | H | | | Z |
| 64 | $CH_3$ | $CH_3$ | 2-(3-$BrC_6H_4CO$) | H | H | | | Z |
| 65 | $CH_3$ | $CH_3$ | 2-(3-$C_2H_5C_6H_4CO$) | H | H | | | Z |
| 66 | $CH_3$ | $CH_3$ | 2-(3,5-di-$CH_3C_6H_3CO$) | H | H | | | Z |
| 67 | $CH_3$ | $CH_3$ | 2-(3-$C_2H_5OC_6H_4CO$) | H | H | | | Z |
| 68 | $CH_3$ | $CH_3$ | 2-(3-$FC_6H_4OCH_2$) | H | H | | | Z |
| 69 | $CH_3$ | $CH_3$ | 2-(2,3-$Cl_2C_6H_3CO$) | H | H | | | Z |
| 70 | $CH_3$ | $CH_3$ | 2-(2,3-$F_2C_6H_3CO$) | H | H | | | Z |
| 71 | $CH_3$ | $CH_3$ | 2-(2-pyrimidyl-CO) | H | H | | | Z |
| 72 | $CH_3$ | $CH_3$ | 2-(4-pyrimidyl-CO) | H | H | | | Z |
| 73 | $CH_3$ | $CH_3$ | 2-di-$CH_3NCO$ | H | H | | | Z |

TABLE II

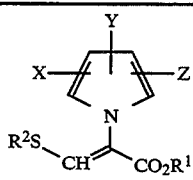

| Compound No. | R¹ | R² | X | Y | Z | Melting point (°C.) | olefinic* | isomer+ |
|---|---|---|---|---|---|---|---|---|
| 1 | $CH_3$ | $CH_3$ | 2-(3-$ClC_6H_4CO$) | H | H | 80 | 7.75 | Z |
| 2 | $CH_3$ | $CH_3$ | 2-$C_6H_5CO$ | H | H | 93–5 | 7.61 | Z |
| 3 | $CH_3$ | $CH_3$ | 2-(4-$FC_6H_4CO$) | H | H | | | Z |

TABLE II-continued

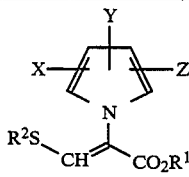

| Compound No. | R¹ | R² | X | Y | Z | Melting point (°C.) | olefinic* | isomer+ |
|---|---|---|---|---|---|---|---|---|
| 4 | CH₃ | CH₃ | 2-(2-C₄H₃S—CO) | H | H | | | Z |
| 5 | CH₃ | CH₃ | 2-C₆H₅OCO | H | H | | | Z |
| 6 | CH₃ | CH₃ | 2-C₆H₄CH₂OCO | H | H | | | Z |
| 7 | CH₃ | CH₃ | 2-C₃H₇OCO | H | H | | | Z |
| 8 | CH₃ | CH₃ | 2-(E—C₆H₅CH=CH) | H | H | | | Z |
| 9 | CH₃ | CH₃ | 2-C₆H₅CH₂CH₂ | H | H | | | Z |
| 10 | CH₃ | CH₃ | 2-C₆H₅CH₂ | H | H | | | Z |
| 11 | CH₃ | CH₃ | 2-(2-C₅H₄N—CO) | H | H | | | Z |
| 12 | CH₃ | CH₃ | 2-C₆H₅S— | H | H | | | Z |

TABLE III

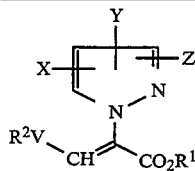

| Compound No. | V | R¹ | R² | X | Y | Z | Melting point (°C.) | olefinic* | isomer+ |
|---|---|---|---|---|---|---|---|---|---|
| 1 | O | CH₃ | CH₃ | 5-(E-4-ClC₆H₄CH=CH) | H | H | 138–9 | 7.62 | Z |
| 2 | O | CH₃ | CH₃ | 5-(E-2,6-di-ClC₆H₃CH=CH) | H | H | 119–121 | 7.75 | Z |
| 3 | O | CH₃ | CH₃ | 5-(E—C₆H₅CH=CH) | H | H | 138 | 7.76 | Z |
| 4 | O | CH₃ | CH₃ | 5-C₆H₅CH₂ | H | H | | | Z |
| 5 | O | CH₃ | CH₃ | 5-C₆H₅CO | H | H | | | Z |
| 6 | O | CH₃ | CH₃ | 5-C₆H₅CH₂OCO | H | H | | | Z |

TABLE IV

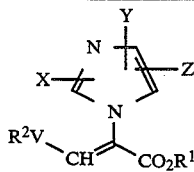

| Compound No. | V | R¹ | R² | X | Y | Z | Melting point (°C.) | olefinic* | isomer+ |
|---|---|---|---|---|---|---|---|---|---|
| 1 | O | CH₃ | CH₃ | 2-C₆H₅CO | H | H | Oil | 7.46 | Z |
| 2 | O | CH₃ | CH₃ | 2-(2-ClC₆H₄CO) | H | H | 159 | 7.57 | Z |
| 3 | O | CH₃ | CH₃ | 2-ⁿC₄H₉ | H | H | Oil | 7.64 | Z |
| 4 | O | CH₃ | CH₃ | 2-(4-ClC₆H₄CO) | H | H | 108–9 | 7.52 | Z |
| 5 | O | CH₃ | CH₃ | 2-(4-FC₆H₄CO) | H | H | 115–117 | 7.54 | Z |
| 6 | O | CH₃ | CH₃ | 2-(4-CH₃C₆H₄CO) | H | H | 103–4 | 7.50 | Z |
| 7 | O | CH₃ | CH₃ | 2-(3,5-Cl₂C₆H₃CO) | H | H | 130–1 | 7.58 | Z |
| 8 | O | CH₃ | CH₃ | 2-(2-C₄H₃S—CO) | H | H | 116–118 | 7.50 | Z |
| 9 | O | CH₃ | CH₃ | 2-(4-C₆H₅—C₆H₄CO) | H | H | | | Z |
| 10 | O | CH₃ | CH₃ | 2-CH₃OCO | H | H | | | Z |
| 11 | O | CH₃ | CH₃ | 2-CN | H | H | | | Z |
| 12 | O | CH₃ | CH₃ | 2-C₆H₅CH₂ | H | H | | | Z |
| 13 | O | CH₃ | CH₃ | 2-(E—C₆H₅CH=CH) | H | H | Oil | 7.44 | Z |
| 14 | O | CH₃ | CH₃ | 2-C₆H₅CH₂CH₂ | H | H | | | Z |
| 15 | O | CH₃ | CH₃ | 2-CH₃ | H | H | 81–2 | 7.65 | Z |
| 16 | O | CH₃ | CH₃ | 2-C₆H₅OCH₂ | H | H | | | Z |
| 17 | O | CH₃ | CH₃ | 2-CH₃ | H | 5-NO₂ | Oil | 7.61 | Z |
| 18 | O | CH₃ | CH₃ | 2-(4-CH₃OC₆H₄CO) | H | H | 140–5 | 7.52 | Z |
| 19 | O | CH₃ | CH₃ | 2-(3-FC₆H₄CO) | H | H | 76–7 | 7.54 | Z |
| 20 | O | CH₃ | CH₃ | 2-C₆H₅S | H | H | 100–1 | 7.50 | Z |
| 21 | O | CH₃ | CH₃ | 2-(3-CH₃OC₆H₄CO) | H | H | | | Z |
| 22 | O | CH₃ | CH₃ | 2-(3-C₄H₃S—CO) | H | H | | | Z |
| 23 | O | CH₃ | CH₃ | 2-(2-C₄H₃O—CO) | H | H | | | Z |
| 24 | O | CH₃ | CH₃ | 2-(3-C₄H₃O—CO) | H | H | | | Z |
| 25 | O | CH₃ | CH₃ | 2-(3-C₅H₄N—CO) | H | H | | | Z |

TABLE IV-continued

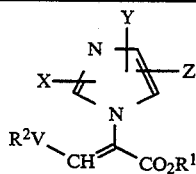

| Compound No. | V | R¹ | R² | X | Y | Z | Melting point (°C.) | olefinic* | isomer+ |
|---|---|---|---|---|---|---|---|---|---|
| 26 | O | $CH_3$ | $CH_3$ | 2-(2-$C_5H_4$N—CO) | H | H | | | Z |
| 27 | O | $CH_3$ | $CH_3$ | 3-(3-$C_2H_5OC_6H_4$CO) | H | H | | | Z |
| 28 | O | $CH_3$ | $CH_3$ | 2-(3-$CNC_6H_4$CO) | H | H | | | Z |
| 29 | O | $CH_3$ | $CH_3$ | 2-(3-$ClC_6H_4$CO) | H | H | | | Z |
| 30 | O | $CH_3$ | $CH_3$ | 2-$C_6H_5OCH_2$CO | H | H | | | Z |
| 31 | O | $CH_3$ | $CH_3$ | 2-(4-$FC_6H_4OCH_2$CO) | H | H | | | Z |
| 32 | O | $CH_3$ | $CH_3$ | 2-(3,5-$F_2C_6H_3$CO) | H | H | | | Z |
| 33 | S | $CH_3$ | $CH_3$ | 2-$C_6H_5$CO | H | H | | | Z |
| 34 | S | $CH_3$ | $CH_3$ | 2-(3-$FC_6H_4$CO) | H | H | | | Z |
| 35 | S | $CH_3$ | $CH_3$ | 2-(3-$CH_3C_6H_4$CO) | H | H | | | Z |
| 36 | S | $CH_3$ | $CH_3$ | 2-(3-$CH_3OC_6H_4$CO) | H | H | | | Z |

TABLE V

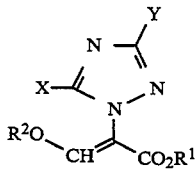

| Compound No. | R¹ | R² | X | Y | Melting point (°C.) | olefinic* | isomer + |
|---|---|---|---|---|---|---|---|
| 1 | $CH_3$ | $CH_3$ | $C_6H_5$ | H | Oil | 7.63 | Z |
| 2 | $CH_3$ | $CH_3$ | (E—$C_6H_5$CH=CH) | H | 116–7 | 7.80 | Z |
| 3 | $CH_3$ | $CH_3$ | $C_6H_5CH_2CH_2$ | H | 65–67 | 7.68 | Z |
| 4 | $CH_3$ | $CH_3$ | $C_6H_5$CO | H | | | Z |
| 5 | $CH_3$ | $CH_3$ | 4F—$C_6H_4$CO | H | | | Z |
| 6 | $CH_3$ | $CH_3$ | $CH_3$OCO | H | | | Z |
| 7 | $CH_3$ | $CH_3$ | $C_6H_5CH_2$ | H | | | Z |
| 8 | $CH_3$ | $CH_3$ | CN | H | | | Z |
| 9 | $CH_3$ | $CH_3$ | 2-$C_4H_3$S—CO | H | | | Z |

*Chemical shift of singlet from olefinic proton on beta-alkoxyacrylate or beta-(alkylthio)-acrylate group. (ppm from tetramethylsilane). Solvent: $CDCl_3$
+Geometry of beta-alkoxyacrylate or beta-(alkylthio)acrylate group. [$C_5H_4N$ = pyridyl, $C_4H_3S$ = thiophenyl, $C_4H_3O$ = furyl, $C_5H_{10}N$ = piperidinyl].

TABLE IA

NMR and Mass Spectral Data

| COMPOUND NO. | |
|---|---|
| 1 | 3.76(3)s, 3.87(3)s, 6.28(1)m, 6.60(2)m, 6.76(2)q, 7.2–7.5(5)m, 7.71(1)s. |
| 2 | 3.72(3)s, 3.85(3)s, 6.31(1)m, 6.82(1)m, 6.90(1)m, 7.4–7.6(3)m, 7.49(1)s, 7.80(2)m. M+ 285. |
| 3 | 3.78(3)s, 3.97(3)s, 6.28(1)q, 6.77(1)m, 6.88(1)m, 7.67(1)s. M+ 206. |
| 9 | 3.77(3)s, 3.92(3)s, 6.6–6.8(2)m, 7.26(1)m, 7.4–7.6(3)m, 7.57(1)s, 7.8–7.9(2)m. |
| 10 | 3.76(3)s, 3.89(3)s, 6.30(1)m, 6.79(1)m, 6.96(1)m, 6.4–6.9(4)q, 7.55(1)s. M+ 319. |
| 11 | 2.16(3)s, 3.76(3)s, 3.87(3)s, 6.10(1)d, 6.78(1)d, 7.4–7.8(5)m, 7.58(1)s. |
| 12 | 3.72(3)s, 3.87(6)d, 6.3(1)m, 6.7–7.0(4)m, 7.46(1)s, 7.8(2)m. M+ 315. |
| 13 | 3.72(3)s, 3.86(3)s, 6.2(1)m, 6.5(1)m, 6.9(1)m, 7.2–7.4(3)m, 7.48(1)s. |
| 14 | 3.74(3), 3.87(3)s, 6.3(1)m, 6.6–7.2(4)m, 7.45(1)s, 7.8(2)m. M+ 303. |
| 15 | 3.70(3)s, 3.83(3)s, 6.2(1)m, 6.6(1)m, 6.8(1)m, 7.0–7.2(3)m, 7.2–7.6(1)m, 7.46(1)s. M+ 303. |
| 16 | 1.35(9)s, 3.69(3)s, 3.52(3)s, 6.25(1)m, 6.8(1)m, 7.3–7.5(4)q, 7.46(1)s. M+ 341 |
| 17 | 3.78(3)s, 3.93(3)s, 6.3(1)m, 6.8(1), 6.9(1)m, 7.55(1)s, 7.8–8.0(4)q. M+ 353. |
| 18 | 3.60(3)s, 3.74(3)s, 6.40(1)m, 6.7(2)m, 6.9(2)m, 7.4(1)m 7.53(1)s, 8.35(1)m. M+ 290. |
| 19 | 3.6(3) broad.s, 3.8(3) broad.s, 6.30(1)m, 6.6(1) broad.s 6.70(1)m, 7.3(1)m, 7.5(1) broad.m, 7.9(1)m, 8.1(1)m, 8.6(1)m. |
| 20 | 3.74(3)s, 3.78(3)s, 3.88(3)s, 6.28(1)m, 6.78(1)m, 7.04(1)m, 7.50(1)s. |
| 21 | 1.37(9)s, 3.70(3)s, 3.82(3)s, 6.2(1)m, 6.7(1)m, 7.0(1)m, 7.40(1)s. M+ 265. |
| 22 | 2.41(3)s, 3.71(3)s, 3.84(3)s, 6.28(1)m, 6.8(1)m, 6.89(1)m, 7.21(2)d, 7.46(1)s, 7.72(2)d. |
| 23 | 3.72(3)s, 3.97(3)s, 6.22(1)q, 6.54(1)m, 6.89(1)m, 7.2–7.4(4)m, 7.46(1)s. M+ 319. |
| 24 | 3.72(3)s, 3.84(3)s, 6.33(1)m, 6.89(1)m, 7.0–7.2(2) 7.47(1)s, 7.57(1)q, 7.77(1)q. M+ 291. |
| 25 | 3.77(3)s, 3.93(3)s, 6.37(1)m, 6.87(1)m, 6.99(1)m, 7.5–7.6(2)m, 7.70(2)d. M+ 353. |
| 26 | 3.77(3)s, 3.92(3)s, 6.29(1)m, 6.58(1)m, 6.97(1)m, 7.32(3)t, 7.57(1)s. |
| 27 | 3.73(3)s, 3.87(3)s, 6.3(1)m, 6.7(1)m, 6.9(1)m, 7.1–7.6(4)m, 7.44(1)s. M+ 303. |
| 28 | 3.72(3)s, 3.85(3)s, 6.3(1)m, 6.8(1)m, 6.9(1)m, 7.2– |

TABLE IA-continued

NMR and Mass Spectral Data

| COMPOUND NO. | |
|---|---|
| | 7.8(4)m, 7.44(1)s. M+ 319. |
| 29 | 0.9(3)t, 1.6(2)m, 3.75(3)s, 3.88(3)s, 6.28(1)m, 6.77(1)m 7.04(1)m, 7.50(1)s. |
| 30 | 1.47(9)s, 3.66(3)s, 3.80(3)s, 6.1(1)m, 6.5(1)m, 6.8(1)m, 7.37(1)s. MH+ 282. |
| 34 | 3.74(3)s, 3.85(3)s, 6.38(1)m, 6.54(1)m, 6.91(1)m 7.05(1)q, 7.47(1)q, 7.50(1)s, 7.62(1)q. |
| 40 | 2.40(3)s, 3.73(3)s, 3.87(3)s, 6.33(1)m, 6.85(1)m, 6.94(1)m, 7.2–7.4(2)m, 7.51(1)s, 7.5–7.8(2)m. |

TABLE IIA

NMR and Mass Spectral Data

| COMPOUND NO. | |
|---|---|
| 1 | 2.37(3)s, 3.76(3)s, 6.38(1)m, 6.87(1)m, 7.00(1)m, 7.3–7.9(5)m, 7.75(1)s. |
| 2 | 2.34(3)s, 3.69(3)s, 6.2(1)m, 6.7(1)m, 6.8(1)m, 7.2–7.8(5)m, 7.61(1)s. MH+ 302. |

TABLE IVA

NMR and Mass Spectral Data

| COMPOUND NO. | |
|---|---|
| 1 | 3.70(3)s, 3.82(3)s, 7.04(1)s, 7.24(1)s, 7.4–7.6(3)m, 7.46(1)s, 8.2–8.3(2)m. M+ 286. |
| 2 | 3.78(3)s, 3.94(3)s, 7.12(1)s, 7.25–7.5(3)m, 7.57(1)s, 7.8(1)m. M+ 320. |
| 3 | 0.8–1.0(3)m, 1.1–1.8(4)m, 2.4–2.6(2)m, 3.76(3)s, 3.94(3)s, 6.74(1)m, 7.02(1)m, 7.64(1)s. |
| 4 | 3.73(3)s, 3.88(3)s, 7.10(1)d, 7.31(1)d, 7.44(2)d, 7.52(1)s, 8.30(2)d. M+ 320. |
| 5 | 3.74(3)s, 3.90(3)s, 7.0–7.4(4)m, 7.54(1)s, 8.42(2)q. M+ 304. |
| 6 | 2.42(3)s, 3.71(3)s, 3.85(3)s, 7.18(1)d, 7.2–7.4(3)m, 7.50(1)s, 8.22(2)d. M+ 300. |
| 7 | 3.78(3)s, 3.94(3)s, 7.17(1)d, 7.39(1)d, 7.58(1)s, 7.59(1)t, 8.30(2)d. M+ 354. |
| 8 | 3.76(3)s, 3.90(3)s, 7.07(1)d, 7.17(1)q, 7.32(1)d, 7.50(1)s, 7.70(1)q, 8.50(1)d. M+ 292. |
| 13 | 3.67(3)s, 3.78(3)s, 6.16(1)d, 6.67(1)d, 6.85(1)d, 7.1–7.4(4)m, 7.44(1)s, 7.4–7.7(2)m. M+ 284. |
| 15 | 2.25(3)s, 3.77(3)s, 3.95(3)s, 6.78(1)s, 7.02(1)s, 7.65(1)s. |
| 17 | 2.28(3)s, 3.81(3)s, 4.02(3)s, 7.61(1)s, 7.73(1)s. M+ 241. |
| 18 | 3.74(3)s, 3.89(3)s, 6.98(2)d, 7.09(1)d, 7.32(1)d 7.52(1)s, 8.39(2)d. M+ 316. |
| 19 | 3.75(3)s, 3.91(3)s, 7.12(1)d, 7.1–7.6(2)m, 7.34(1)d, 7.54(1)s, 7.9–8.3(2)m. M+ 304. |
| 1 | 3.68(3)s, 3.84(3)s, 7.4–7.7(5)m, 7.63(1)s, 8.08(1)s. M+ 259. |
| 2 | 3.77(3)s, 3.96(3)s, 6.68(1)d, 7.3–7.6(5)m, 7.77(1)d, 7.80(1)s, 8.04(1)s. MH+ 285. |
| 3 | 2.7–3.2(4)m, 3.76(3)s, 3.95(3)s, 7.1–7.4(5)m, 7.68(1)s, 7.98(1)s. M+ 287. | key:
pp from tetramethylsilane; (integral),s—singlet, d—doublet, t—triplet, q—quartet, m—multiplet.
M+—Mass spectrum molecular ion.

The compounds of the invention having the general formula (I) can be prepared from substituted heterocyclic compounds of general formula (II) by the steps shown in Scheme I.

Throughout Scheme I the terms A, B, E, D, $R^1$ and $R^2$ are as defined above, and L is a leaving group such as a halogen (iodine, bromine or chlorine) atom.

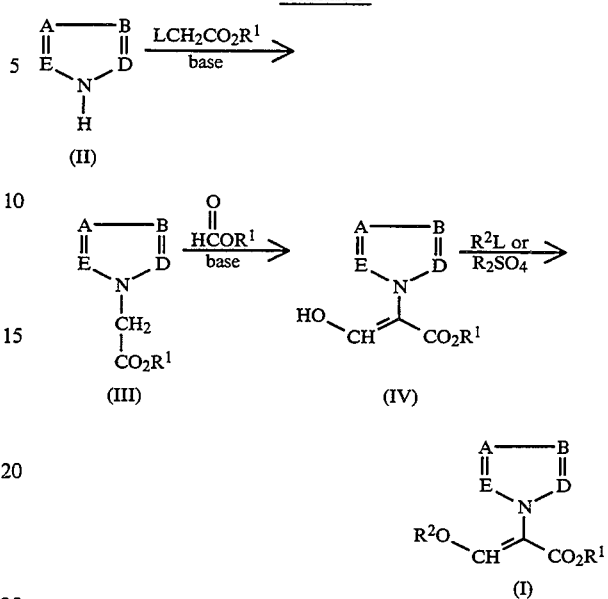

Scheme I

Compounds of general formula (IV) can be prepared by treatment of substituted acetic esters of general formula (III) with a base and a formic ester such as methyl formate or $HCO_2R^1$ wherein $R^1$ is as defined above, in a suitable solvent. If the reaction is quenched with a suitable species of general formula $R^2L$ or $R_2{}^2SO_4$ wherein $R^2$ is as defined above but is not hydrogen and L is a leaving group such as a halogen atom, compounds of general formula (I) may be obtained.

Alternatively, compounds of general formula (IV) may be isolated by quenching the reaction with water or an acid. In such cases, conversion into compounds of general formula (I) is performed in a separate step by treatment with a suitable base (such as sodium carbonate or potassium carbonate) and a suitable reagent of general formula $R^2L$ or $R_2{}^2SO_4$, wherein $R^2$ and L are as defined above, in a suitable solvent.

Alternatively, alkali metal salts of compounds of general formula (IV) may be isolated and converted into compounds of general formula (I) by treatment with a suitable reagent of general formula $R_2L$ or $R_2{}^2SO_4$, wherein $R^2$ and L are as defined above in a suitable solvent, as a subsequent step.

Compounds of general formula (III) can be prepared by treatment of heterocyclic compounds of general formula (II) with a suitable base such as sodium hydride and a substituted acetic ester of general formula $LCH_2CO_2R^1$ wherein $R^1$ and L are as defined above, in a suitable solvent.

Compounds of general formula (I) in which —$OR^2$— is a group —$SR^2$ where S is sulphur may be obtained by treating compounds of general formula (IV) with a suitable reagent of general formula $R^2SO_2Cl$ wherein $R^2$ is defined above, in a suitable solvent and then quenching with a reagent of general formula $NaSR^2$ e.g. sodium methanethiolate.

Compounds of general formula (II) can be prepared by standard methods described in the chemical literature. For example, heterocyclic compounds of general formula (II), in which each of A, B and D is the group =CH— and E is the group =CZ— wherein Z is (E)—Aryl—CH=CH, may be prepared via the Wittig reaction between the appropriate phosphorane and the 2-formylpyrrole (see, for example, R A Jones, T Pojarlieva and R J Heal, *Tetrahedron*, 1968, 24, 2013, and references therein).

Compounds of general formula (II) in which each of A, B and D is the group =CH— and E is the group =CZ— wherein Z is ArylCO—, may be prepared via the Vilsmeier-Haack reaction of the appropriate benzamide and the appropriate pyrrole in phosphoryl chloride (see, for example, G McGillivray and J White, *J.Org.Chem.* 1977, 42, 4248, and references therein).

Compounds of general formula (II) in which both B and D are the group =CH—, A is the group =N—, and E is the group =CZ— wherein Z is ArylCO—, may be prepared by the reaction of the appropriate benzoylchloride and imidazole in a suitable base (see, for example, L. A. M. Bastiaansen and E. F. Godefroi, *Synthesis*, 1982, 675, and references therein).

Compounds of general formula (III) in which each of A, B and D is the group =CH— and E is the group =CZ— wherein Z is defined above, may be prepared from the reaction of the appropriate 2,5-dimethoxytetrahydrofuran and the appropriate esters of glycine in a suitable solvent such as acetic acid (see, for example, C W Jefford and W Johncock, *Helv Chim Acta*, 1983, 2661, and references therein).

Compounds of general formula (III) in which B is the group =CH— and each of A and D is the group =N— and E is the group =CZ— wherein Z is Aryl may be prepared by the reaction of the appropriate acylamidine and the appropriately substituted hydrazine in a suitable solvent such as acetic acid to form a triazole ring (see, for example, Yang-i Lin et al., *J.Org.Chem.*, 1979, 44, 4160, and references therein).

The compounds of formula I and compositions containing them, are variously active against a wide range of fungal diseases, particularly, for example, against *Pyricularia oryzae* on rice

*Puccinia recondita, Puccinia striformis* and other rusts on wheat, *Puccinia hordei, Puccinia striiformis* and other rusts on barley, and rusts on other hosts e.g. coffee, pears, apples, vegetables and ornamental plants *Erysiphe graminis* (powdery mildew) on barley and wheat and other powdery mildews on various hosts such as *Spaerotheca macularis* on hops.

*Sphaerothaea fuliginea* on cucurbits (e.g. cucumber) *Podosphaera leucotricha* on apples and *Uncinula necator* on vines *Helminthosporium* spp., *Rhynchosporium* spp. and *Pseudocercosporellaherpotrichoides* on cereals *Cercospora arachidicola* and *Cercosporidum personata* on peanuts and other *Cercospora* species on for example sugar beet, bananas and soya beans and rice. *Botrytis cinerea* (grey mould) on tomatoes, strawberries, vegetables, vines and other hosts *Alternaria* species on vegetables (e.g. cucumber, oil-seed rape, apples, tomatoes and other hosts). *Venturia inaequalis* (scab) on apples and *Plasmopara viticola* (downy mildew) on vines.

Other downy mildews such as *Bremia lactucae* on lettuce, *Peronospora* spp. on soybeans, tobacco, onions and other hosts and *Pseudoperonospora humuli* on hops and *Pseudoperonospora cubensis* on cucurbits *Phytophthora infestans* on potatoes and tomatoes and other *Phytophthora* spp. on vegetables, strawberries, avocado, pepper, ornamentals, tobacco, cocoa and other hosts. *Thanatephorus cucumeris* on rice and other *Rhhizoctonia* species on various hosts such as wheat and barley, vegetables, cotton and turf.

Some of the compounds have also shown a broad range of activities against fungi in vitro. They have activity against various post-harvest diseases of fruit (e.g. *Penicillium digitatum* and *italicum* and *Trichoderma viride* on oranges and *Gloesporium musarum* on bananas).

Further some of the compounds are active as seed dressings against *Fusarium* spp., *Septoria* spp., *Tilletia* spp. (bunt, a seed borne disease of wheat), *Ustilago* spp., *Helminthosporium* spp. on cereals, *Rhizoctonia solani* on cotton and *Pyricularia oryzae* on rice.

The compounds can move acropetally in the plant tissue. Moreover, the compounds can be volatile enough to be active in the vapour phase against fungi on the plant.

The compounds may also be useful as industrial (as opposed to agricultural) fungicides, e.g. in the prevention of fungal attack on wood, hides, leather and especially paint films.

This invention, therefore, includes the foregoing uses of the compounds (and compositions containing them) in addition to their principal use as plant fungicides.

The compounds may be used as such for fungicidal purposes but are more conveniently formulated into compositions for such usage. The invention thus provides a fungicidal or plant growth regulating composition comprising a compound of general formula (I) as hereinbefore defined, and, optionally, a carrier or diluent.

The invention also provides a method of combating fungi, which comprises applying to a plant, to seed of a plant, or to the locus of the plant or seed, a compounds as hereinbefore defined, or a composition containing the same.

The compounds, can be applied in a number of ways. For example they can be applied, formulated or unformulated, directly to the foliage of a plant, to seeds or to other medium in which plants are growing or are to be planted. They can be sprayed on, dusted on or applied as a cream or paste formulation, or they can be applied as a vapour or as slow release granules. Application can be to any part of the plant including the foliage, stems, branches or roots, or to soil surrounding the roots, or to the seed before it is planted; or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal methods of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example fillers such as kaolin, bentonits, kieselguhr, dolomite, calcium carbonate, talc, powdered magnesia, Fuller's earth, gypsum, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example a mineral oil) for assisting the adhesion of the composition to the seed; alternatively the active ingredient can be formulated for seed dressing purposes using an organic solvent (for example N-methylpyrrolidone, propylene glycol or dimethylformamide). The compositions may also be in the form of wettable powders or water dispersible granules comprising wetting or dispersing agents to facilitate their dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as isophorone, cyclohexanone and methylcyclohexanone, chlorinated hydrocarbons such as chlorobenzene and trichlorethane, and alcohols such as furfuryl alcohol, butanol and glycol ethers.

Suspension concentrates of largely insoluble solids may be prepared by ball or bead milling with a dispersing agent and including a suspending agent to stop the particles of the solid settling.

Compositions to be used as sprays may be in the form of aerosols wherein the formulation is held in a container under pressure in the presence of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I) or a salt or metal complex thereof.

Wettable powders, emulsifiable concentrates and suspension concentrates will normally contain surfactants e.g. a wetting agent, dispersing agent, emulsifying agent or suspending agent. These agents can be cationic, anionic or non-ionic agents.

Suitable cationic agents are quaternary ammonium compounds, for example cetyltrimethylammonium bromide. Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as olely or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending-agents are hydrophilic colloids (for example polyvinylpyrrolidone and sodium carboxymethylcellulose), and swelling clays such as bentonits or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10-85%, for example 25-60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, e.g. compounds having a similar or complementary fungicidal activity or plant posses plant growth regulating, herbicidal or insecticidal activity.

A fungicidal compound which may be present in the composition of the invention may be one which is capable of combating ear disease of cereals (e.g. wheat) such as *Septoria, Gibberella* and *Helminthosporium* spp., seed and soil borne diseases and downy and powdery mildews on grapes and powdery mildew and scab on apple etc. By including another fungicide, the composition can have a broader spectrum of activity than the compound of general formula (I) alone. Further to the other fungicide can have a synergistic effect on the fungicidal activity of the compound of general formula (I). Examples of fungicidal compounds which may be included in the composition of the invention are carbendazim, benomyl, thiphanate-methyl, thiabendazole, fuberidazole, etridazole, dichlorofluanid, cymoxanil, oxadixyl, ofurace, metalaxyl, furalaxyl, benalaxyl, fosetyl aluminjure, fenarimol, iprodione, procymidone, vinclozolin, penconazole, myclobutanil, R0151297, S3308, pyrazophos, ethirimol, ditalimfos, tridemorph, triforine, nuarimol, triazbutyl, guazatine, propiconazole, prochloraz, flutriafol, chlortriafol i.e. the chemical 1-(1, 2,4-triazol-1-yl)-2-(2,4-dichlorophenyl)-hexan-2-ol, DPX H6573(1-((bis-4-fluorophenyl)methylsilyl)-methyl)-1H-1,2,4-triazole, triadimefon, triadimenol, diclobutrazol, fenpropimorph, fenpropidine, chlorozolinate, diniconazol, imazalil, fenfuram, carboxin, oxycarboxln, methfuroxam, dodemorph, BAS 454, blasticidin S, kasugamycin, edifenphos, kitazin P, cycloheximide, phthalide, probenazole, isoprothiolane, tricyclazole, pyroquilan, chlorbenzthiazone, neoasozin, polyoxin D, validamycin A, repronil, flutolanil, pencycuron, diclomezine, phenazin oxide, nickel dimethyldithiocarbamate, techlofthalam, bitertanol, bupirimate, etaconazole, streptomycin, cypofuram, biloxazol, quinomethionate, dimethirimol, 1- (2-cyano-2-methoxyimino-acetyl)-3-ethyl urea, fenapanil, tolclofosmethyl, pyroxyfur, polyram, maneb, mancozeb, captafol, chlorothalonil, anilazine, thiram, captan, folpet, zineb, propineb, sulphur, dinocap, binapactryl, nitrothalisopropyl, dodine, dithianon, fentin hydroxide, fentin acetate, tecnazene, quintozene, dichloran, copper containing compounds such as copper oxychloride, copper sulphate and Bordeaux mixture, and organomercury compounds.

The compounds of general formula (I) can be mixed with soil, peat or other rooting media for the protection of plants against seed-borne, soil-borne or foliar fungal diseases.

Suitable insecticides which may be incorporated in the composition of the invention include pirimicarb, dimethoate, demeton-s-methyl, formothion, carbaryl, isoprocarb, XMC, BPMC, carbofuran, carbosulfan, diazinon, fenthion, fenitrothion, phenthoate, chlorpyrifos, isoxathion, propaphos, momocrotophas, buprofezin, ethroproxyfen and cycloprothrin.

Plant growth regulating compounds are compounds which control weeds or seedhead formation, or selectively control the growth of less desirable plants (e.g. grasses).

Examples of suitable plant growth regulating compounds for use with the invention compounds are the gibberellins (e.g. $GA_3$, $GA_4$ or $GA_7$), the auxins (e.g. indoleacetic acid, indolebutyric acid, naphthoxyacetic acid or naphthylacetic acid), the cytokinins (e.g. kinetin, diphenylurea, benzimidazole, benzyladenine or benzylaminopurine), phenoxyacetic acids (e.g. 2,4-D or MCPA), substituted benzoic acids (e.g. triiodobenzoic acid), morphactins (e.g. chlorfluoroecol), maleic hydrazide, glyphosate, glyphosine, long chain fatty alcohols and acids, dikegulac, paclobutrazol, flurprimidol, fluoridamid, mefluidide, substituted quaternary ammonium and phosphonium compounds (e.g. chloromequat chlorphonium or mepiquatchloride), ethephon, carbetamide, methyl-3,6-dichloroanisate, daminozide, asulam, abscisic acid, isopyrimil, 1-(4-chlorophenyl)-4,6-dimethyl-2-oxo-1,2-dihydropyridine-3-carboxylic acid, hydroxybenzonitriles (e.g. bromoxynil), difenzoquat, benzoylprop-ethyl 3,6-dichloropicolinic acid, fenpentezol, inabenfide, triapenthenol and tecnazene.

The following Examples illustrates the invention. Throughout these examples, magnesium sulphate was used to dry solutions, and reactions involving water-sensitive intermediates were performed under an atmosphere of nitrogen.

EXAMPLE 1

This Example illustrates the preparation of (Z)-methyl 3-methoxy-2-[(E)-2-styrylpyrrol-1-yl]acrylate (Compound No. 1 of Table I).

Sodium hydride (2.4 g, 0.05 mol of 50% dispersion in oil) was washed with petrol 40°-60° and suspended in dry tetrahydrofuran, (THF 50 ml). Pyrrole-2-carboxaldehyde (4.75 g, 0.05 mol) in THF (25 ml) was added dropwise over 1 hour at room temperature. After a further 1½ hours benzyltriphenylphoephoniuxn chloride (19.5 g, 0.05 mol) was added portionwise (solution becomes red, exotherm) and it was stirred for 3 hours at 50° C. The mixture was concentrated under reduced pressure, water was added to the residue and it was extracted with diethyl ether. After drying with magnesium sulphate and evaporation a viscous red oil resulted. Purification by column chromatography using silica gel with petroleum ether 60°-80°: diethyl ether (1:1) as the eluent gave a waxy solid (5.3 g). This was recrystallised from petrol 60°-80°: chloroform to give (M)-2-styrylpyrrole (1.5 g) as a crystalline solid which is unstable to light.

Sodium hydride (0.3 g, 0.0063 mol) was washed with petrol 60°-80° and suspended in dimethylformamide (DMF, 25 ml). The (E)-2-styrylpyrrole (1.0 g, 0.006 mol) in DMF (10 ml) was added dropwise at room temperature. After stirring for 1½ hours, methyl bromoacetate (0.56 ml, 0.006 mol) in DMF (5 ml) was added dropwise. After 16 hours it was poured into water (200 ml) and extracted with ether (3×100 ml). The extracts were washed with brine dried and evaporated under reduced pressure to give a brown oil. Purification by column chromatography using silica gel with ethyl acetate: petrol 60°-80°, (1:1) as the eluent gave methyl (2-styrylpyrrol-1-yl)acetate (0.5 g, 30% yield) as a buff amorphous solid.

Sodium hydride (0.63 g, 0.013 mol) was washed with petrol 60°-80° and suspended in DMF (30 ml) under nitrogen. To this methyl (2-styrylpyrrol-1-yl)acetate (1.6 g, 0.0066 mol) and methyl formate (8.2 ml, 0.13 mol) in DMF (10 ml) was added dropwise at room temperature. After 4 hours it was poured into 200 ml of saturated sodium bicarbonate, extracted with diethyl ether (2×100 ml), then the aqueous layer was neutralised with concentrated hydrochloric acid and extracted again with diethyl ether (2'100 ml). This was washed with brine, dried and evaporated to give methyl 3-hydroxy-2-[(E)-2-styrylpyrrol-1-yl]acrylate (2.0 g) as an orange-yellow oil. This was used in the following reaction without further purification.

To a stirred suspension of potassium carbonate (1.8 g, 0.013 mol) in DMF (50 ml) the methyl 3-hydroxy-2-[(E)-2-styrylpyrrol-1-yl]acrylate (2.0 g, 0.0074 mol) in DMF (20 ml) was added dropwise. After stirring for 2 hours at room temperature, dimethyl sulphate (0.63 ml, 0.0067 mol) was added dropwise (slight exotherm). This was stirred for 16 hours then poured into saturated sodium bicarbonate solution (200 ml) and extracted with diethyl ether (2×100 ml). The extracts were washed with brine, dried and evaporated under reduced pressure to give a viscous orange oil. Purification by column chromatography using silica gel with diethyl ether: petrol 60°-80°, (1:1) as the eluent gave the tile compound (700 mg, 37% yield) as a pale yellow solid melting at 126°-8° C.

EXAMPLE 2

This Example illustrates the preparation of (Z)methyl 3-methoxy-2-[2-benzoylpyrrol-1-yl ]acrylate (Compound No. 2 of Table I).

Potassium tert-butoxide (7.22, 0.064 mol) was dissolved in DMF (40 ml) and 2-benzoylpyrrole (10 g, 0.058 mol) in DMF (10 ml) was added dropwise with stirring at room temperature. This was left for 16 hours then cooled to 0° C. when methyl bromoacetate (5.4 ml, 0.058 mol) in DMF (5 ml) was added dropwise. The reaction mixture was stirred for 16 hours then poured into water (150 ml) and extracted with diethyl ether (2×100 ml). The extracts were washed with brine (2×75 ml) dried and evaporated to give methyl (2-benzoylpyrrol-1-yl)acetate (12.6 g, 89%) as a brown oil which crystallised on standing.

Sodium hydride (1.44 g, 55% in oil, 0.033 mol) was washed with petrol 60°-80° and suspended in DMF (15 ml). To this the methyl (2-benzoylpyrrol-1-yl)acetate (4.0 g, 0.0165 mol) in DMF (15 ml) and methyl formate (20.3 ml, 0.33 mol) was added dropwise at room temperature. After 4 hours it was poured into 200 ml of 10% potassium carbonate, washed with diethyl ether (2×100 mls), then the aqueous was neutralised with concentrated hydrochloric acid and extracted with diethyl ether (2×100 ml). These extracts were washed with brine, dried and evaporated to give methyl 3-hydroxy-2- (2-benzoylpyrrol-1-yl)acrylate (3.86 g, 86%) as a white crystalline solid melting at 112°–113°.

To a stirred suspension of potassium carbonate (5.0 g, 0.037 mol) in DMF (50 ml) the methyl 3-hydroxy-2-(2-benzoyl-pyrrol-1-yl)acrylate (5.0 g, 0.0185 mol) in DMF (10 ml) was added dropwise. After stirring for 2 hours at room temperature, dimethyl sulphate (1.75 ml, 0.0185 mol) was added dropwise (slight exotherm). This was stirred for 3 hours then poured into saturated sodium bicarbonate solution (200 ml) and extracted with diethyl ether (2×100 ml). The extracts were washed with brine, dried and evaporated under reduced pressure to give a viscous orange oil. Purification by column chromatography using silica gel with ethyl acetate as the eluent gave the title compound (3.7 g, 70%) a white crystalline solid melting at 78°–79° C. See Table IA for NMR and mass spectral data.

EXAMPLE 3

This Example illustrates the preparation of (Z)-methyl 3-methylthio-2-[2-(3-chlorobenzoyl)pyrrol-1-yl]-acrylate (Compound No. 1 of Table II).

To a solution of methyl 3-hydroxy-2-[2-(3-chlorobenzoyl)pyrrol-1-yl]acrylate (2.14 g, 0.007 mol, obtained using the same procedure as Example 2) in triethylamine (1.1 ml, 0.008 mol) and dichloromethane (40 ml) at 0° C., methanesulphonyl chloride (0.6 ml, 0.077 mol) was added dropwise at 0° C. After 2 hours, sodium methanethiolate (0.5 g, 0.0071 mol) was added and the mixture stirred for 16 hours. This was poured into aqueous sodium hydroxide solution (75 ml, 10%), the organic phase was separated and washed with water then dried and evaporated under reduced pressure to give a brown oil. Purification by medium pressure column chromatography using silica gel with diethyl ether as the eluant gave the title compound (1.4 g, 60%) as a buff crystalline solid melting at 80° C. See Table IIA for NMR data.

EXAMPLE 4

This Example illustrates the preparation of (Z)-methyl 3-methoxy-2-[5-phenyl-1,2,4-triazol-1-yl]acrylate (Compound No. 1 of Table V).

N-[(Dimethylamino)methylene]benzamide (2.0 g, 0.011 mol) and methyl hydrazine acetate hydrochloride salt (1.9 g, 0.011 mol) were warmed in acetic acid at 90° C. for 1½ hours. The acetic acid was evaporated under reduced pressure and the residue neutralised with saturated aqueous sodium bicarbonate, then extracted into chloroform (2×100 ml) washed with water, dried and evaporated under reduced pressure to give methyl [5-phenyl-1,2,4-triazol-1-yl]acetate as a clear oil (2.3 g, 96%).

Sodium hydride (0.88 g, 0.018 mol, 50% dispersion in oil) was washed with dry petrol 40°–60° and suspended in DMF (15 ml). A mixture of methyl [5-phenyl-1,2,4-triazol-1-yl]-acetate (2.0 g, 0.009 mol) and methyl formate (11.4 ml, 0.18 mol) in DMF (15 ml) was added at room temperature with stirring over 10 minutes. After 2 hours aqueous potassium carbonate (200 ml, 10%) was added and the aqueous layer extracted with diethyl ether (2×100 ml), then the aqueous layer was neutralised with concentrated hydrochloric acid and then extracted with ethyl acetate (3×150 ml). The ethyl acetate extract was washed with brine and dried then evaporated under reduced pressure to give methyl 3-hydroxy-2-[5-phenyl-1,2,4-triazol-1-yl acrylate (2.2 g) as a yellow oil.

To a stirred suspension of potassium carbonate (2.6 g, 0.018 mol) in DMF (25 ml) the methyl 3-hydroxy-2-[5-phenyl-1,2,4-triazol-1-yl]acrylate (2.2 g, 0.009 mol) in DMF (10 ml) was added dropwise. After stirring for 1½ hours at room temperature, dimethyl sulphate (0.87 ml, 0.009 mol) was added (slight exotherm). This was stirred for 3 hours then poured into water (150 ml) and extracted with ethyl acetate (3×75 ml). The extracts were washed with brine, dried and evaporated under reduced pressure to give a clear oil. Purification by column chromatography using silica gel with ethyl acetate as the eluant gave the title compound (1.5 g, 64%) as a clear oil. See Table VA for NMR and mass spectrum data.

EXAMPLE 5

This Example illustrates the preparation of (Z)-methyl 3-methoxy-2 - (pyrrol-1-yl)acrylate (Compound No. 55 of Table I).

A solution of the hydrochloride salt of the methyl ester of glycine (6.30 g) and potassium acetate (8.00 g) in water (10 ml) was added to glacial acetic acid (50 ml). The resulting mixture was heated to reflux, 2,5-dimethoxytetrahydrofuran (6.60 g) was added in one portion, and heating under reflux was continued for 4 hours. After cooling, the reaction mixture was neutralised with sodium bicarbonate and extracted with ethyl acetate. The extracts were washed with water, dried, concentrated under reduced pressure, and distilled at 125° C. and ca. 15 torr using a short-path distillation apparatus to give methyl pyrrol-1-ylacetate (2.62 g, 38% yield) as a colourless liquid, infra red (film) 1750 cm$^{-1}$.

A solution of methyl pyrrol-1-ylacetate (2.00 g) in methyl formate (4.4 ml) was added dropwise to a stirred suspension of sodium hydride (0.38 g) in dry toluene (10 ml) cooled in an ice bath. The mixture was allowed to warm to room temperature, 2 drops of dry methanol were added (effervescence), and it was heated slowly to 50° C. whereupon the mixture became at first clear, then deposited a thick off-white solid. The mixture was heated at 50° C. for 30 minutes, allowed to cool and diluted with ether. The solid was filtered off, washed with ether and partially dried to give a white solid (3.12 g), infrared (film) 1665, 1650 cm$^{-1}$. Methyl iodide (0.93 ml) was added in one portion to a stirred suspension of this solid in DMF (20 ml). After stirring at room temperature for 2 hours, the mixture was poured into water and extracted with ether. The extracts were washed with water, dried and concentrated to give a white solid (2.35 g) which was triturated with petrol and dried to give the title compound (1.73 g, 66% yield) as a white solid, melting point 88°–89° C., infrared (nujol mull) 1700, 1635 cm$^{-1}$, proton nmr (CDCl$_3$) delta: 3.77 (3H,singlet); 3.91 (3H, singlet); 6.26 (2H,triplet J 5 Hz), 6.69 (2H,triplet J 5 Hz); 7.51 (1H, singlet) ppm. NOTE : On treatment with trichloroacetyl chloride and 2,6-dimethylpyridine in refluxing chloroform, and then, in a subsequent step, with potassium carbonate in propan-1-ol, the title compound was converted into (Z)-methyl 3-methoxy-2-[(2-prop-1-yloxycarbonyl)pyrrol-1-yl ]acrylate, compound No. 29 of Table I.

EXAMPLE 6

An emulsifiable concentrate is made up by mixing the ingredients, and stirring the mixture until all the constituents are dissolved.

| | |
|---|---|
| Compound No 2 of Table I | 10% |
| Isophorone | 25% |
| Calcium dodecylbenzenesulphonate | 5% |
| Nonylphenolethoxylate (13 moles ethylene oxide) | 10% |
| Alkyl benzenes | 50% |

EXAMPLE 7

The active ingredient is dissolved in methylene dichloride and the resultant liquid sprayed onto the granules of attapulgite clay. The solvent is then allowed to evaporate to produce a granular composition.

| | |
|---|---|
| Compound No 11 of Table I | 5% |
| Attapulgite granules | 95% |

EXAMPLE 8

A composition suitable for use as a seed dressing is prepared by grinding and mixing the three ingredients.

| | |
|---|---|
| Compound No 14 of Table I | 50% |
| Mineral oil | 2% |
| China clay | 48% |

EXAMPLE 9

A dustable powder is prepared by grinding and mixing the active ingredient with talc.

| | |
|---|---|
| Compound No 14 of Table I | 5% |
| Talc | 95% |

EXAMPLE 10

A suspension concentrate is prepared for chemicals which are largely insoluble solids by ball milling, for example, the constituents set out below, to form an aqueous suspension of the ground mixture with water.

| | |
|---|---|
| Compound No 2 of Table I | 40% |
| Sodium lignosulphonate | 10% |
| Bentonite clay | 1% |
| Water | 49% |

This formulation can be used as a spray by diluting into water or applied directly to seed.

EXAMPLE 11

A wettable powder formulation is made by mixing together the ingredients set out below and then grinding the mixture until all are thoroughly mixed.

| | |
|---|---|
| Compound No 11 of Table I | 25% |
| Sodium lauryl sulphate | 2% |
| Sodium lignosulphonate | 5% |
| Silica | 25% |
| China clay | 43% |

EXAMPLE 12

A Col formulation was prepared by ball-milling the constituents set out below and then forming an aqueous suspension of the ground mixture with water.

| | |
|---|---|
| Compound No 14 of Table I | 40% |
| "Dispersol" T | 10% |
| "Lubrol" APN5 | 1% |
| Water | |

EXAMPLE 13

A dispersible powder formulation was made by mixing together the ingredients set out below and then grinding the mixture until all were thoroughly mixed.

| | |
|---|---|
| Compound No 11 of Table I | 25% |
| "Aerosol" OT/B | 2% |
| "Dispersol" A.C. | 5% |
| China clay | 28% |
| Silica | 40% |

In Examples 6 to 13 the proportions of the ingredients given are by weight. The remaining compounds of Tables I, II, III, IV and V were all similarly formulated as for Examples 6 to 13.

There now follows an explanation of the compositions or substances represented by the various Trade Marks and Trade Names mentioned above.

DISPERSOL T & AC : a mixture of sodium sulphate and a condensate of formaldehyde with sodium naphthalene sulphonate LUBROL APN5 : a condensate of nonyl phenol (1 mole) with naphthalene oxide (5.5 moles)

AEROSOL OT/B : dioctyl alkyl naphthalene sulphonate

EXAMPLE 14

The compounds were tested against a variety of foliar fungal diseases of plants. The technique employed was as follows.

The plants were grown in John Innes Potting Compost (No 1 or 2) in 4 cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredient) were sprayed on to the foliage and applied to the roots of the plants in the soil. The sprays were applied to maximum retention and the root drenches to a final concentration equivalent to approximately 40 ppm a.i./dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:
4=no disease
3=trace—5% of disease on untreated plants
2=6-25% of disease on untreated plants
1=26-59% of disease on untreated plants
0=60-100% of disease on untreated plants
The results are shown in Tables VI-IX.

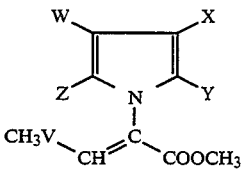

or a stereoisomer thereof, wherein W, X and Y are independently hydrogen, halogen, nitro, cyano, $C_{1-4}$ alkyl, $C_{3-6}$ alkenyl, $C_{3-6}$ alkynyl, $C_{1-4}$ alkoxy, amino, $COOR^3$, $CONR^3R^4$, $COR^3$, $S(O)_nR^3$ or $CR^3=NR^4$, where $R^3$ and $R^4$ are hydrogen or $C_{1-4}$ alkyl and n is 0,

TABLE VI

| COMPOUND NUMBER | PUCCINIA RECONDITA (WHEAT) | ERYSIPHE GRAMINIS (BARLEY) | VENTURIA INAEQUALIS (APPLE) | PYRICULARIA ORYZAE (RICE) | CERCOSPORA ARACHIDICOLA (PEANUT) | PLASMOPARA VITICOLA (VINE) | PHYTOPHTHORA INGESTANS (TOMATO) |
|---|---|---|---|---|---|---|---|
| 1 | 4 | 0 | 4 | 4 | 4 | 4 | — |
| 2 | 4 | 4 | 4 | 4 | 2 | 4 | — |
| 3 | 0 | 4 | 4 | 3 | 4 | 4 | — |
| 9 | 0 | 0 | 2 | 0 | 0 | 2 | — |
| 10 | 3 | 4 | 3 | 3 | 4 | 4 | — |
| 11 | 4 | 4 | — | 4 | 4 | 4 | — |
| 12 | 2 | 0 | 1 | 0 | 0 | 4 | — |
| 13 | 3 | 3 | 4 | 4 | 4 | 4 | — |
| 14 | 4 | 4 | 4 | 4 | 4 | 4 | — |
| 15 | 4 | 4 | — | 4 | 3 | 4 | — |
| 16 | 0 | 0 | 1 | 0 | 0 | 0 | — |
| 18 | 0 | 1 | 1 | 0 | 0 | 0 | — |
| 20 | 4 | 4 | 4 | 4 | 4 | 4 | — |
| 21 | 2 | 4 | 4 | 0 | 4 | 0 | — |
| 22 | 3 | 4 | 4 | 3 | 0 | 4 | — |
| 23 | 3 | 4 | 4 | 4 | 4 | 4 | — |
| 24 | 4 | 4 | 4 | 4 | 4 | 4 | — |
| 25 | 2 | 4 | 2 | 3 | 4 | 4 | — |
| 26 | 0 | 1 | 2 | 0 | 4 | 0 | — |
| 27 | 4 | 4 | 4 | 4 | 4 | 4 | — |
| 28 | 4 | 4 | 4 | 4 | 4 | 4 | 3 |
| 29 | 4 | 4 | 4 | 4 | 4 | 4 | — |
| 30 | 4 | 4 | 4 | 3 | 4 | 4 | 2 |
| 34 | | | | | | | |
| 40 | | | | | | | |

TABLE VIII

| COMPOUND NUMBER | PUCCINIA RECONDITA (WHEAT) | ERYSIPHE GRAMINIS (BARLEY) | VENTURIA INAEQUALIS (APPLE) | PYRICULARIA ORYZAE (RICE) | CERCOSPORA ARACHIDICOLA (PEANUT) | PLASMOPARA VITICOLA (VINE) | PHYTOPHTHORA INGESTANS (TOMATO) |
|---|---|---|---|---|---|---|---|
| 1 | 1 | 0 | 0 | 0 | — | 0 | — |

TABLE IX

| COMPOUND NUMBER | PUCCINIA RECONDITA (WHEAT) | ERYSIPHE GRAMINIS (BARLEY) | VENTURIA INAEQUALIS (APPLE) | PYRICULARIA ORYZAE (RICE) | CERCOSPORA ARACHIDICOLA (PEANUT) | PLASMOPARA VITICOLA (VINE) | PHYTOPHTHORA INGESTANS (TOMATO) |
|---|---|---|---|---|---|---|---|
| 1 | 4 | 3 | 4 | 4 | 4 | 4 | — |
| 2 | 0 | 0 | 4 | 0 | 4 | 0 | — |
| 3 | 0 | 3 | 1 | 0 | 0 | 0 | — |
| 5 | 4 | 4 | 4 | 4 | 4 | 3 | 3 |
| 6 | 0 | 0 | 4 | 0 | 0 | 3 | — |
| 7 | 1 | 0 | 4 | 3 | 4 | 3 | 2 |
| 8 | 2 | 0 | 4 | 4 | 4 | 3 | 0 |
| 15 | 0 | 0 | 0 | 0 | 0 | 3 | 0 |
| 18 | 1 | 0 | 0 | 0 | 4 | 2 | 0 |

— means not tested

We claim:
1. A compound of formula:

1 or 2; Z is $COOR'$, $CONR'R''$ or $COR'$, were $R''$ is hydrogen or $C_{1-4}$ alkyl, $R'$ is thienyl which is optionally substituted with $C_{1-4}$ alkyl, $C_{1-4}$ alkoxy, halogen, halo($C_{1-4}$)alkyl, $C_{3-6}$ cycloalkyl, $C_{3-6}$ cycloalkenyl, phenyl, cyano or nitro; and V is oxygen or sulphur.

2. A compound according to claim 1 wherein Z is COR' and R' is thienyl optionally substituted with $C_{1-4}$ alkyl, $C_{1-4}$ alkoxy, halogen, halo($C_{1-4}$)alkyl, $C_{3-6}$ cycloalkyl, $C_{3-6}$ cycloalkenyl, phenyl, cyano or nitro.

3. A fungicidal composition comprising, as an active ingredient, a fungicidally effective amount of a compound of general formula I as defined in claim 1, together with a carrier therefor.

4. A process for combating fungi which comprises applying to a plant, to seed of a plant, or to the locus of the plant or seed, a fungicidally effective amount of a compound as defined in claim 1 or a composition containing the same.

5. A compound of formula:

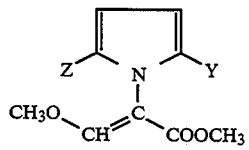

wherein Z is theinylcarbonyl; and Y is hydrogen, $C_{1-4}$ alkyl or nitro.

6. A compound of formula:

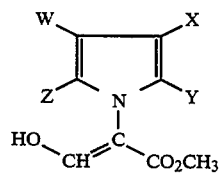

in which W, X and Y are independently hydrogen, halogen, nitro, cyano, $C_{1-4}$ alkyl, $C_{3-6}$ alkenyl, $C_{3-6}$ alkynyl, $C_{1-4}$ alkoxy, amino, $COOR^3$, $CONR^3R^4$, $COR^3$, $S(O)_nR^3$ or $CR^3{=}NR^4$, where $R^3$ and $R^4$ are hydrogen or $C_{1-4}$ alkyl and n is 0, 1 or 2; Z is COOR', CONR'R" or COR', where R" is hydrogen or $C_{1-4}$ alkyl, R' is thienyl, which is optionally substituted with $C_{1-4}$ alkyl, $C_{1-4}$ alkoxy, halogen, halo($C_{1-4}$)alkyl, $C_{3-6}$ cycloalkyl, $C_{3-6}$ cycloalkenyl, phenyl, cyano or nitro.

* * * * *